(12) United States Patent
Voskoboynikov et al.

(10) Patent No.: US 8,609,567 B2
(45) Date of Patent: Dec. 17, 2013

(54) OCP CATALYST WITH IMPROVED STEAM TOLERANCE

(75) Inventors: Timur V. Voskoboynikov, Arlington Heights, IL (US); Aleksey Y. Pelekh, Woodridge, IL (US); John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 570 days.

(21) Appl. No.: 12/639,577

(22) Filed: Dec. 16, 2009

(65) Prior Publication Data

US 2011/0143919 A1    Jun. 16, 2011

(51) Int. Cl.
 *B01J 29/06* (2006.01)
(52) U.S. Cl.
 USPC ............... 502/60; 502/63; 502/64; 502/71; 502/77
(58) Field of Classification Search
 USPC ................... 502/60, 63, 64, 71, 77
 See application file for complete search history.

(56) References Cited

U.S. PATENT DOCUMENTS

| | | | | |
|---|---|---|---|---|
| 4,283,306 A | * | 8/1981 | Herkes | 502/202 |
| 4,542,117 A | * | 9/1985 | Morris et al. | 502/66 |
| 4,544,793 A | * | 10/1985 | Okado et al. | 585/640 |
| 4,585,799 A | * | 4/1986 | Morris et al. | 518/717 |
| 4,623,636 A | * | 11/1986 | Young | 502/232 |
| 4,721,827 A | * | 1/1988 | Cullo et al. | 585/467 |
| 5,182,012 A | | 1/1993 | Miller | |
| 2001/0031903 A1 | * | 10/2001 | Hotier et al. | 585/475 |
| 2005/0080307 A1 | * | 4/2005 | Voskoboynikov et al. | 585/648 |
| 2006/0084568 A1 | | 4/2006 | Filimonov | |
| 2007/0032379 A1 | * | 2/2007 | Ito et al. | 502/213 |
| 2009/0143629 A1 | * | 6/2009 | Voskoboynikov | 585/314 |
| 2010/0105974 A1 | * | 4/2010 | Towler et al. | 585/651 |

FOREIGN PATENT DOCUMENTS

| | | | |
|---|---|---|---|
| EP | 109060 A1 | | 5/1984 |
| EP | A 0134333 | * | 3/1985 |
| EP | 0 229 952 | * | 7/1987 |
| EP | 565789 A1 | | 10/1993 |
| EP | 1685897 A2 | | 8/2006 |
| EP | 2460784 A1 | | 6/2012 |

OTHER PUBLICATIONS

European Search Report dated Oct. 29, 2013 for Application No. 10842382.3-1352/2512666 PCT/US2010045299.

* cited by examiner

*Primary Examiner* — Elizabeth Wood
(74) *Attorney, Agent, or Firm* — Arthur E Gooding

(57) ABSTRACT

A catalyst is present for use in an olefin cracking process. The catalyst is a zeolite that has been loaded with an alkaline earth metal. The alkaline earth metal loaded catalyst has an increased steaming tolerance and increases the useful life of the catalyst during the cracking process and the regeneration cycle.

15 Claims, No Drawings

OCP CATALYST WITH IMPROVED STEAM TOLERANCE

FIELD OF THE INVENTION

This invention relates to the cracking of olefins. In particular, this invention relates to improvements in catalyst for use in olefin cracking, where the catalyst has a high steam tolerance.

BACKGROUND OF THE INVENTION

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces essentially all of the ethylene and propylene. While hydrocarbons used as feedstock for light olefin production include natural gas, petroleum liquids, and carbonaceous materials including coal, recycled plastics or any organic material, an important source is naphtha where larger paraffins and naphthenes are cracked to produce olefins.

One means of producing ethylene and propylene is an olefin cracking process, where larger olefins in the C4 to C8 range are cracked to produce propylene and ethylene in high propylene to ethylene ratios. Typically, an olefin cracking process is integrated with a naphtha cracking unit, and the propylene is dramatically increased. The use of an olefin cracking unit can take lower value C4 to C6 byproducts to produce additional propylene and ethylene.

The olefin cracking process uses a catalyst that deactivates during regeneration. This leads to replacement of the catalyst when regeneration no longer sufficiently reactivates the catalyst.

SUMMARY OF THE INVENTION

The present invention is directed to an improved catalyst having a greater tolerance to steaming. The catalyst is a zeolite that is loaded with an alkaline earth metal after normal preparation. The zeolite is loaded with the alkaline earth metal to an amount between 0.1 wt % and 2 wt % of the total catalyst weight. A preferred alkaline earth metal is magnesium or calcium.

Other objects, advantages and applications of the present invention will become apparent to those skilled in the art from the following drawing and detailed description.

DETAILED DESCRIPTION OF THE INVENTION

Light olefins demand is growing. The primary production of light olefins is through cracking, either steam or catalytic cracking, and produces a product mix of ethylene and propylene. Adjustments in operating conditions, and the types of catalysts used can influence the relative amounts of propylene and ethylene produced. It is desirable to increase the light olefins yields because of the increased demand. One method of increasing yields is the addition of an olefins cracking process (OCP) for the production of light olefins from heavier, and less valuable, olefins.

The olefin cracking process could be integrated with other refinery processes, such as a naphtha cracker for increasing the production of light olefins. Light olefins of commercial value are propylene and ethylene. The OCP process produces coke on the catalyst, and the catalyst needs to be periodically regenerated by burning off the coke. The OCP catalyst slowly deactivates during the regeneration due to the presence of hydrogen on the coke, which leads to formation of water vapor. In addition, the catalyst is susceptible to deactivation during the olefin cracking process. Deactivation can occur when oxygen-containing compounds are present in the feed. Oxygen containing compounds include alcohols, ethers, ketones, and other oxygenates that can be generated in upstream processes as by-products, or occur in the feedstream. Modifying the catalyst to have a high steam tolerance is therefore very important for a steady propylene production and plant operation. Improving the steam tolerance improves the life of the catalyst, and allows for more regeneration cycles.

Currently, the active component of the OCP catalyst is Silicalite zeolite, treated by steam and acid-washed. Silicalite is in H-form and contains only traces of other charge balancing cations, such as $Na^+$. The present invention found that modification of the OCP catalyst with magnesium improves catalyst steam tolerance. The present invention comprises treating an olefin cracking zeolite with an alkaline earth element, and then calcining the alkaline earth element loaded zeolite. For most catalysts in the petrochemical industry, the presence of alkali or alkaline earth elements is detrimental to the activity of the catalyst. However, in the instant invention, the loading of an alkaline earth element was found to substantially slow the loss of activity in an environment with steam.

The alkaline earth elements are selected from one or more of magnesium (Mg), calcium (Ca), strontium (Sr), and barium (Ba). Preferred alkaline earth elements are magnesium and calcium. The alkaline earth elements are loaded onto the zeolite in an amount 0.1 wt. % and 2 wt. % of the total catalyst weight, with a preferred amount between 0.5 wt. % and 1 wt. %.

A preferred zeolite is silicalite, with the silicalite having a silica to alumina ratio greater than 200, and a preferred ratio of silica to alumina greater than 400.

The olefin cracking process subjects the catalyst to steam, which contributes to the deactivation of the catalyst. Experimental aging of the catalyst through exposure to steaming resulted in a loss of activity. The conventional OCP catalyst and a catalyst loaded with 0.6 wt % Mg were subjected to steaming conditions. The steaming conditions included a 2.3 vol. % $H_2O$ in $N_2$ at 585° C. In the following table, the activities, in arbitrary units, are compared. The data shows that the loading of the alkaline earth element substantially slows the rate of deactivation of the catalyst, such that the life of a catalyst modified with magnesium could be substantially extended.

TABLE

| | Catalyst Activity | |
|---|---|---|
| Steaming duration (days) | Conventional catalyst | Mg-doped catalyst |
| 0 | 3.786 | 3.696 |
| 14 | 1.276 | 3.476 |
| 28 | | 2.364 |
| 42 | | 1.834 |
| 43 | 0.832 | |
| 56 | | 1.475 |

In one embodiment, the catalyst can further include a binder. The binder is present in the catalyst is an amount between 10% and 75% by weight of the total catalyst weight. The binder is used to confer hardness and strength on the catalyst. Examples of binder materials include, but are not limited to, alumina, silica, aluminum phosphate, silica-alumina, zirconia, titania, and mixtures thereof. In referring to the types of binders that may be used, it should be noted that the term silica-alumina does not mean a physical mixture of silica and alumina but means an acidic and amorphous material that has been cogelled or coprecipitated. In this respect, it is possible to form other cogelled or coprecipitated amorphous materials that will also be effective as binder materials. These include silica-magnesias, silica-zirconias, silica-thorias, silica-berylias, silica-titanias, silica-alumina-thorias, silica-alumina-zirconias, aluminophosphates, mixtures of these, and the like. Other binders include other refractory oxides and clays such as montmorillonite, kaolin, palygorskite, smectite, attapulgite, kaolinite, saponite, and bentonite. While many binders are possible, a preferred binder is silica.

Optionally, the catalyst can be subject to further treatment, wherein the catalyst is subject to a finishing steaming treatment. The finishing steaming step is performed to improve the catalyst selectivity. The catalyst can be further treated to an acid. Acid washing of a catalyst can remove non-framework alumina to make for a more active catalyst.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A catalyst having a longer life for cracking olefins comprising:
    a zeolite comprising silicalite having a silica to alumina ratio greater than 200 that is steam treated and acid washed and then loaded with an alkaline earth metal; and
    the alkaline earth metal loaded zeolite is calcined.

2. The catalyst of claim 1 wherein the zeolite has a silica to alumina ratio of greater than 400.

3. The catalyst of claim 1 wherein the alkaline earth metal is selected from the group consisting of magnesium (Mg), calcium (Ca), strontium (Sr), barium (Ba), or mixtures thereof.

4. The catalyst of claim 3 wherein the alkaline earth metal is selected from the group consisting of magnesium, calcium and mixtures thereof.

5. The catalyst of claim 1 wherein the alkaline earth metal loading is between 0.1 wt % and 2 wt. % of the catalyst.

6. The catalyst of claim 5 wherein the alkaline earth metal loading is between 0.5 wt. % and 1 wt. %.

7. The catalyst of claim 1 further comprising a binder in an amount between 10% and 75% by weight of the total catalyst weight.

8. The catalyst of claim 7 wherein the binder comprises silica.

9. A catalyst having a longer life for cracking olefins comprising:
    a silicalite with a silica to alumina ratio of greater than 200 that is loaded with magnesium; and
    the magnesium loaded silicalite is calcined;
    wherein the catalyst is further subjected to a finishing steam treatment.

10. The catalyst of claim 9 wherein the magnesium loading is between 0.5 wt % and 1 wt. % of the catalyst.

11. The catalyst of claim 9 wherein the zeolite has a silica to alumina ratio of greater than 400.

12. The catalyst of claim 9 further comprising a binder in an amount between 10% and 75% by weight of the total catalyst weight.

13. The catalyst of claim 12 wherein the binder comprises silica.

14. The catalyst of claim 9 further comprising acid washing of the catalyst.

15. A catalyst having a longer life for cracking olefins comprising:
    a silicalite with a silica to alumina ratio of greater than 200 that is loaded with magnesium; and
    the magnesium loaded silicalite is calcined;
    wherein the catalyst is further subjected to acid wash.

* * * * *